US007985720B2

(12) United States Patent
Kramer et al.

(10) Patent No.: US 7,985,720 B2
(45) Date of Patent: Jul. 26, 2011

(54) MULTICOLORED CLEANSING BAR AND METHOD FOR THE USE THEREOF

(76) Inventors: Bruce Elliot Kramer, Potomac, MD (US); Joy Elizabeth Belin, Potomac, MD (US)

( * ) Notice: Subject to any disclaimer, the term of this patent is extended or adjusted under 35 U.S.C. 154(b) by 323 days.

(21) Appl. No.: 10/787,142

(22) Filed: Feb. 27, 2004

(65) Prior Publication Data

US 2005/0192191 A1 Sep. 1, 2005

(51) Int. Cl.
*A61K 7/50* (2006.01)

(52) U.S. Cl. ......... 510/141; 510/152; 510/146; 510/155

(58) Field of Classification Search .................. 510/141, 510/146, 144, 152
See application file for complete search history.

(56) References Cited

U.S. PATENT DOCUMENTS

| | | | | |
|---|---|---|---|---|
| 4,017,573 | A * | 4/1977 | Joshi | 510/146 |
| 4,017,574 | A * | 4/1977 | Joshi | 510/146 |
| 4,083,796 | A | 4/1978 | Schubert et al. | |
| 4,695,395 | A | 9/1987 | Caswell et al. | |
| 4,996,000 | A | 2/1991 | Redeker | |
| 5,300,249 | A | 4/1994 | Schwartz et al. | |
| 5,510,050 | A | 4/1996 | Dunbar et al. | |
| 5,681,980 | A | 10/1997 | Beerse et al. | |
| 6,121,216 | A | 9/2000 | Narath et al. | |
| 6,147,040 | A | 11/2000 | van der Hagen | |
| 6,214,780 | B1 | 4/2001 | Narath et al. | |
| 6,376,441 | B1 | 4/2002 | Ross et al. | |
| 6,383,999 | B1 | 5/2002 | Coyle et al. | |
| 6,390,797 | B1 | 5/2002 | Myers | |
| 6,555,509 | B2 | 4/2003 | Abbas et al. | |
| 6,673,756 | B2 * | 1/2004 | Sonnenberg et al. | 510/141 |
| 2003/0053972 | A1 | 3/2003 | Newell | |
| 2003/0199405 | A1 | 10/2003 | Abbas et al. | |

* cited by examiner

*Primary Examiner* — Necholus Ogden, Jr.

(57) ABSTRACT

A multicolored cleansing bar includes at least one cleansing material, wherein the cleansing bar includes a plurality of layers, wherein the plurality of layers includes at least a red layer, an orange layer, a yellow layer, a green layer, a blue layer, and a purple layer. A method for improving a child's hygiene includes (1) providing a child with a multicolored cleansing bar including a cleansing material and having a plurality of colors, and (2) having the child wash or bathe with the cleansing bar, wherein the child is motivated to wash or bathe with the cleansing bar in order to see the appearance of the cleansing bar change.

17 Claims, 3 Drawing Sheets

MULTICOLORED CLEANSING BAR AND METHOD FOR THE USE THEREOF

FIELD OF THE INVENTION

The present invention relates to a multicolored cleansing bar and to a method for the use thereof. More particularly, the present invention relates to a multicolored cleansing bar having a plurality of layers and to a method for improving a child's hygiene by using a multicolored cleansing bar.

BACKGROUND OF THE INVENTION

The spread of germs among children is a major problem today, causing suffering for children, absence from school, increased healthcare expenses, and lost sleep for parents.

This problem could be significantly reduced by increasing the amount of hand washing done by children, because hand washing is an effective means for maintaining good hygiene and preventing the spread of germs and illness.

However, while children are among the people at highest risk of getting sick, they are also the least likely to wash their hands and wash them well.

Children everywhere need constant reminders from adults to wash their hands, but this easily turns into nagging, which is tiresome for both the adults and the children. Also, parents may remind children, but do not have the time to supervise and ensure the hand washing is being done well.

Thus, another technique is needed to promote adequate hand washing among children and thereby reduce the spread of germs and disease.

SUMMARY OF THE INVENTION

One object of the present invention is to provide a cleansing bar which will motivate a child to improve his or her hygiene. Another object of the present invention is to provide a method which will motivate a child to improve his or her hygiene. These and other objects are satisfied by the present invention.

In one embodiment, the present invention provides a multicolored cleansing bar comprising at least one cleansing material, wherein the cleansing bar comprises a plurality of layers, wherein the plurality of layers comprises at least a red layer, an orange layer, a yellow layer, a green layer, a blue layer, and a purple layer. By providing a child with such a cleansing bar, the child is motivated to wash or bathe sufficiently, because the child wishes to see the color of the cleansing bar change, and the color of the cleansing bar will change more quickly the more the child washes or bathes with the cleansing bar.

In another embodiment, the present invention provides a method for improving a child's hygiene, comprising (1) providing a child with a multicolored cleansing bar comprising a cleansing material and having a plurality of colors, and (2) having the child wash or bathe with the cleansing bar, wherein the child is motivated to wash or bathe with the cleansing bar in order to see the appearance of the cleansing bar change. By providing a child with a cleansing bar having a plurality of colors as in the method of the present invention, the child is motivated to wash or bathe sufficiently, because the child wishes to see the appearance of the cleansing bar change, and the appearance of the cleansing bar will change more quickly the more the child washes or bathes with the cleansing bar. As a result, the child's hygiene is improved.

DETAILED DESCRIPTION OF THE INVENTION

Figure 1:
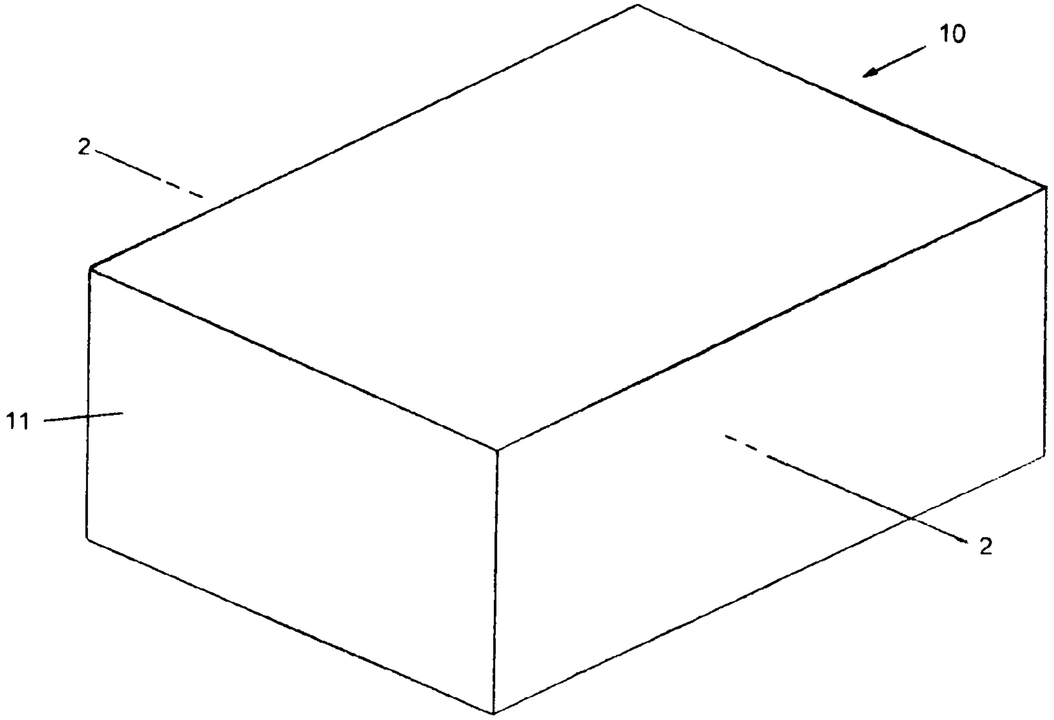
FIG. 1 is an embodiment of the present invention in which the cleansing bar has an outside layer.

The cleansing material used in the present invention can be a soap or a synthetic detergent system well known in the art. In this regard, suitable examples can be found in the disclosures of U.S. Pat. Nos. 4,695,395, 5,300,249, 5,510,050, 5,681,980, 6,121,216, 6,214,780, 6,383,999, and 6,673,756, which describe various soaps and synthetic detergent systems and which are incorporated herein by reference. An antibacterial compound, such as triclocarban, can be added in an effective amount. As an example, the antibacterial compound can be added in an amount of 0.2-2.0% by wt., particularly 1.2% by wt.

The colors for the multicolored cleansing bar are provided by coloring agents such as color dyes or pigment materials well known in the art, suitable for use in a cleansing bar and not harmful to human skin, and can be incorporated into the bar in a manner well known in the art. In this regard, suitable examples can be found in the disclosures of U.S. Pat. No. 4,083,796, which describes a dye system for soap and synthetic detergent bars, and U.S. Pat. No. 4,017,574, which describes a process for making multicolored soap bars, and both of these patents are incorporated herein by reference.

For example, the coloring agent can be a water soluble dye certified by the Food & Drug Administration for external cosmetic or drug use, i.e., FD&C, D&C or external D&C dyes. Suitable examples include FD&C Red No. 4, D&C Red No. 17, D&C Red No. 19, D&C Red No. 33, FD&C Red No. 40, D&C Orange No. 4, FD&C Yellow No. 5, FD&C Yellow No. 6, D&C Yellow No. 8, D&C Yellow No. 10, D&C Yellow No. 11, FD&C Green No. 3, D&C Green No. 5, D&C Green No. 8, FD&C Blue No. 1, D&C Violet No. 2, and ext. D&C Violet No. 2. The coloring agent can also be selected from materials such as chromium hydroxide green, chromium oxide greens, and ultramarines (ultramarine blue). To add sparkle to the cleansing bar, mica can be used, and to provide lighter colors or a white colored cleansing material, titanium dioxide can be used.

A single coloring agent or a system comprising more than one coloring agent can be used to provide a desired color, and suitable examples include the following. A purple cleansing material can be provided with, e.g., ext. D&C Violet No. 2. As an alternative for providing a purple cleansing material, U.S. Pat. No. 4,083,796 discloses a dye system including D&C Green No. 5 and D&C Red No. 19 to provide a deeply hued purple soap. A lighter purple cleansing material can be provided by, e.g., a system including titanium dioxide, D&C Violet No. 2, and D&C Red No. 17. A blue cleansing material can be provided with, e.g., FD&C Blue No. 1 or ultramarine blue, or it can be provided by, e.g., a system including ext. D&C Violet No. 2 and D&C Green No. 5 or a system including ultramarine blue and FD&C Green No. 3. A green cleansing material can be provided by, e.g., a system including FD&C Yellow No. 5 and FD&C Green No. 3, or a system including D&C Green No. 8 and FD&C Green No. 3. A yellow cleansing material can be provided with FD&C Yellow No. 5, or it can be provided by, e.g., a system including D&C Yellow No. 10 and FD&C Red No. 4. An orange cleansing material can be provided with D&C Orange No. 4, or it can be provided by, e.g., a system including FD&C Red No. 40 and FD&C Yellow No. 5. A light orange cleansing material can be provided by, e.g., a system including D&C Red No. 17, titanium dioxide, and D&C Yellow No. 11. A red cleansing material can be provided by, e.g., a system including FD&C Red No. 40 and D&C Red No. 33 or a system including FD&C Red No. 4 and D&C Red No. 33.

The coloring agent can be dispersed, suspended, dissolved or emulsified in a meltable solid vehicle to provide a coloring material that when combined with the cleansing material results in an attractive colored cleansing material. The coloring material can comprise from about 1 to about 50 percent by weight, preferably from about 10 to about 20 percent by weight, of the coloring agent depending on the color effect that is desired. The weight ratio of colored material to cleansing material can be 1:50 to 1:1000, preferably 1:100 to 1:200, depending on the colors used and the effect desired. In a particular embodiment, the colored material can be used in an amount of about 1 to 2 percent by weight depending on the colors used and the effect desired.

To improve a child's hygiene, the colors in the cleansing bar can be present in any manner which would motivate the child to wash or bathe more, particularly, a manner in which the appearance of the cleansing bar changes so that the child is pleased by the new appearance. For example, the colors can be present in a variegated, striated or marbleized manner, such as in U.S. Pat. No. 4,017,574. In one preferred embodiment, at least 3 different colors are used. In another preferred embodiment, at least four different colors are used. In still another preferred embodiment, at least five colors are used. In yet another preferred embodiment, at least six colors are used.

In a preferred embodiment, the colors are present in a plurality of layers. Preferably, the plurality of layers comprises at least a red layer, an orange layer, a yellow layer, a green layer, a blue layer, and a purple layer. These layers approximate the colors of a rainbow, i.e., red, orange, yellow, green, blue, indigo and violet. A rainbow-like set of colors is desirable, because children like rainbows. To enhance the surprise effect of the color change from one layer to the next, the layers can be translucent or, preferably, opaque.

FIG. 1 shows a first embodiment of the present invention, in which a cleansing bar 10 has an outside layer 11. The outside layer 11 may have a logo or other design thereon.

Figure 2:
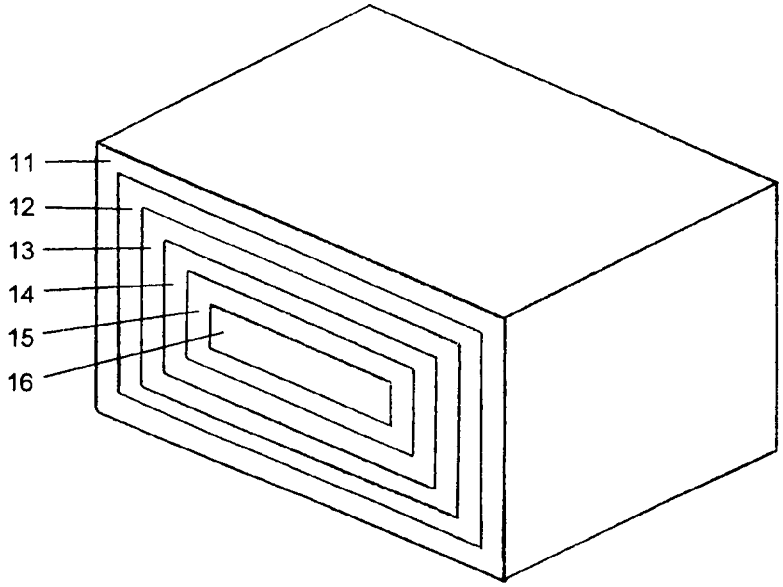
FIG. 2 is a cross section of the cleansing bar of FIG. 1.

FIG. 2 shows a cross section of the cleansing bar of FIG. 1 along line 2-2. The cleansing bar comprises an outside layer 11, a second layer 12 which is adjacent to the outside layer 11, a third layer 13 which is adjacent to the second layer 12, a fourth layer 14 which is adjacent to the third layer 13, a fifth layer 15 which is adjacent to the fourth layer 14, and a sixth layer 16 which is adjacent to the fifth layer 15.

In one preferred embodiment, the outside layer 11 is red. In another preferred embodiment, the outside layer 11 is purple.

In the preferred embodiment where the outside layer 11 is red, it is preferred that the second layer 12 is orange, the third layer 13 is yellow, the fourth layer 14 is green, the fifth layer 15 is blue, and the sixth layer 16 is purple.

In the preferred embodiment where the outside layer 11 is purple, it is preferred that the second layer 12 is blue, the third layer 13 is green, the fourth layer 14 is yellow, the fifth layer 15 is orange, and the sixth layer 16 is red.

Figure 3:
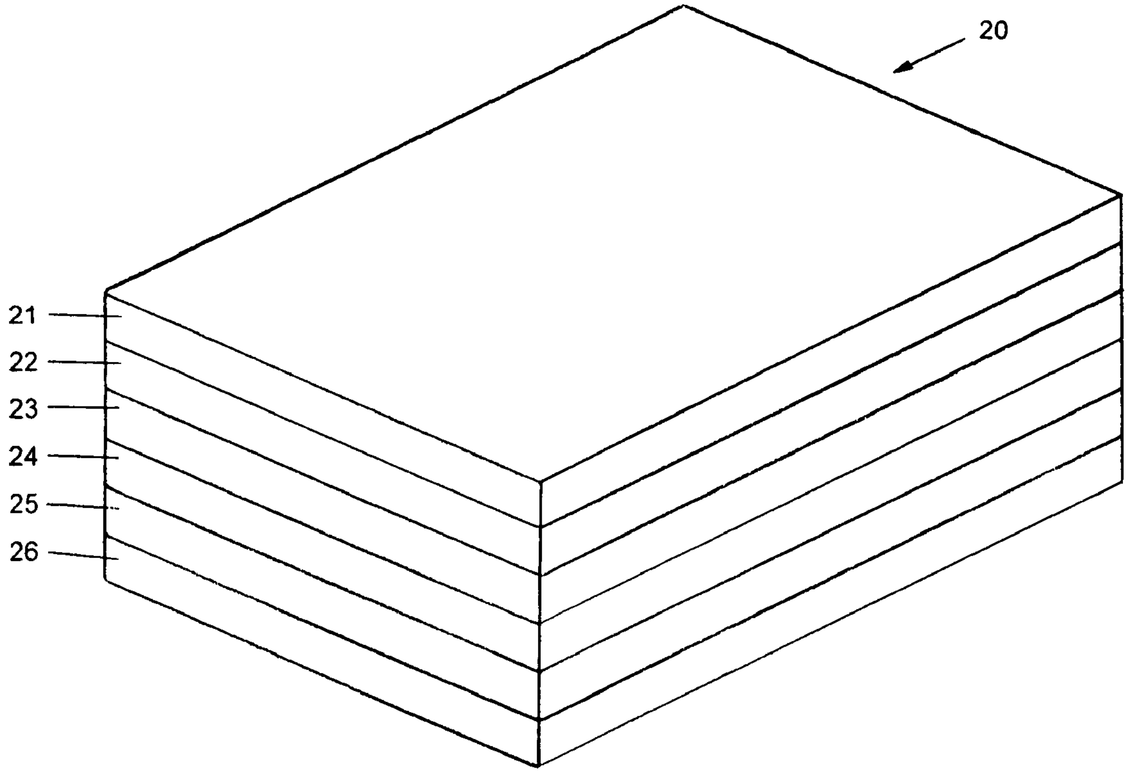
FIG. 3 is an embodiment of the present invention in which the cleansing bar has a top layer.

FIG. 3 shows a second embodiment of the present invention, in which a cleansing bar 20 comprises a top layer 21, a second layer 22 which is adjacent to the top layer 21, a third layer 23 which is adjacent to the second layer 22, a fourth layer 24 which is adjacent to the third layer 23, a fifth layer 25 which is adjacent to the fourth layer 24, and a sixth layer 26 which is adjacent to the fifth layer 25. The top layer 21 may have a logo or design thereon.

In one preferred embodiment, the top layer 21 is red. In another preferred embodiment, the top layer 21 is purple.

In the preferred embodiment where the top layer 21 is red, it is preferred that the second layer 22 is orange, the third layer 23 is yellow, the fourth layer 24 is green, the fifth layer 25 is blue, and the sixth layer 26 is purple.

In the preferred embodiment where the top layer 21 is purple, it is preferred that the second layer 22 is blue, the third layer 23 is green, the fourth layer 24 is yellow, the fifth layer 25 is orange, and the sixth layer 26 is red.

In the preferred embodiment where the top layer is red, the second layer is orange, the third layer is yellow, the fourth layer is green, the fifth layer is blue, and the sixth layer is purple, the cleansing bar can further comprise a seventh layer which is adjacent to the sixth layer and is blue, an eighth layer which is adjacent to the seventh layer and is green, a ninth layer which is adjacent to the eighth layer and is yellow, a tenth layer which is adjacent to the ninth layer and is orange, and an eleventh layer which is adjacent to the tenth layer and is red.

In the preferred embodiment where the top layer is purple, the second layer is blue, the third layer is green, the fourth layer is yellow, the fifth layer is orange, and the sixth layer is red, the cleansing bar can further comprise a seventh layer which is adjacent to the sixth layer and is orange, an eighth layer which is adjacent to the seventh layer and is yellow, a ninth layer which is adjacent to the eighth layer and is green, a tenth layer which is adjacent to the ninth layer and is blue, and an eleventh layer which is adjacent to the tenth layer and is purple.

Figure 4:
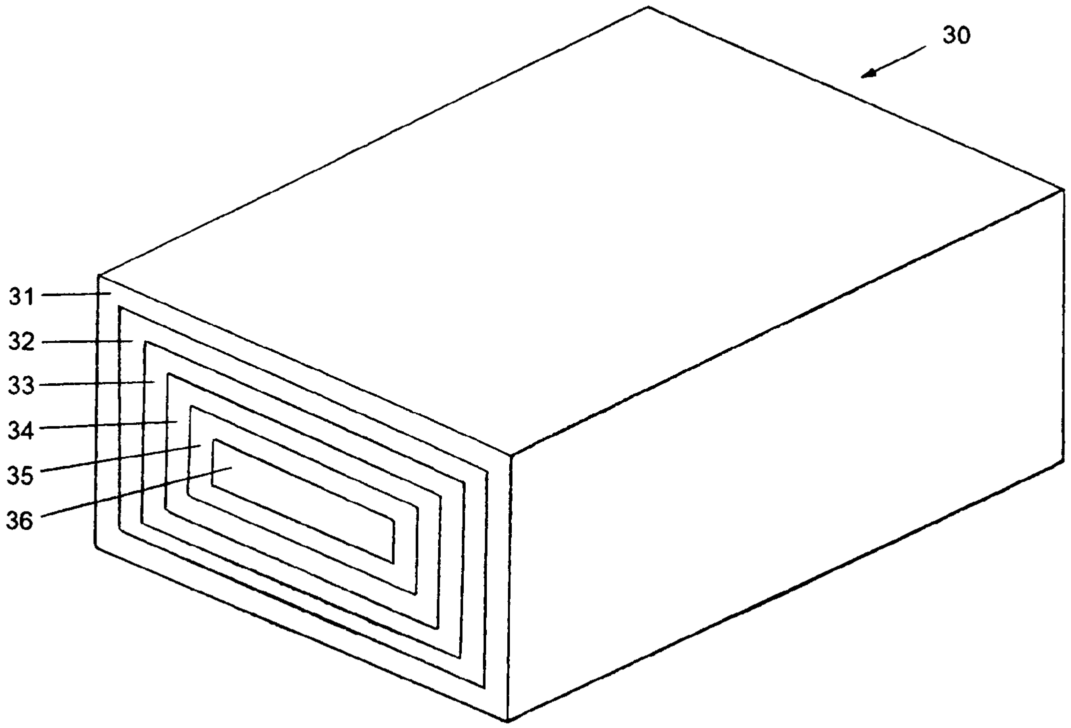
FIG. 4 is an embodiment of the present invention in which the cleansing bar has a first layer which is at all of the top, bottom, and both sides of the bar, but not all of the front and back of the bar.

FIG. 4 shows a third embodiment of the present invention, in which the cleansing bar 30 has a top, bottom, two sides, front and back, and comprises a first layer 31 which is at all of the top, bottom, and both sides of the bar, but not all of the front and back of the bar, a second layer 32 which is adjacent to the first layer 31, a third layer 33 which is adjacent to the second layer 32, a fourth layer 34 which is adjacent to the third layer 33, a fifth layer 35 which is adjacent to the fourth layer 34, and a sixth layer 36 which is adjacent to the fifth layer 35. The first layer 31 may have a logo or design thereon.

In one preferred embodiment, the first layer 31 is red. In another preferred embodiment, the first layer 31 is purple.

In the preferred embodiment where the first layer 31 is red, it is preferred that the second layer 32 is orange, the third layer 33 is yellow, the fourth layer 34 is green, the fifth layer 35 is blue, and the sixth layer 36 is purple.

In the preferred embodiment where the first layer 31 is purple, it is preferred that the second layer 32 is blue, the third layer 33 is green, the fourth layer 34 is yellow, the fifth layer 35 is orange, and the sixth layer 36 is red.

The cleansing bar of the present invention can be made by a method for making cleansing bars known in the art. For example, the cleansing bar can be made by melt casting, or it can be made by extrusion. Suitable examples can be found in the disclosures of U.S. Pat. Nos. 4,017,574, 6,376,441, 6,383,999, and 6,555,509, as well as in U.S. Published Patent Application No. 2003/0199405, all of which describe methods for making cleansing bars and all of which are incorporated herein by reference.

In one suitable molding operation, a first molten material for a first colored layer (which can ultimately be, e.g., a top layer) can be poured into a mold and allowed to harden, then a second molten material for a second colored layer can be poured onto the first colored layer in the mold and allowed to harden, and so on, until the desired multilayered cleansing bar is formed, and then the bar can be ejected from the mold.

In another molding operation, a first molten material for a first colored layer can be poured into a mold, allowed to harden, and then removed. Then, a second molten material for a second colored layer can be poured into a second, larger mold, and the first colored layer can be added thereto at an appropriate time, such that when hardening occurs the second colored layer surrounds the first colored layer. This type of procedure can be continued until the desired outside layer is formed.

In another suitable molding operation, in a manner similar to that described in U.S. Pat. No. 6,376,441, a removable divider can be used to define a first cavity in a mold, a first molten material for a first colored layer can be poured into the first cavity and allowed to harden, and then the divider can be removed to provide a first colored layer with an exposed surface, then a removable divider can be used to define a second cavity in the mold with the exposed surface of the first colored layer, a second molten material for a second colored layer can be poured into the second cavity and allowed to harden, and then the divider can be removed to provide a second colored layer with an exposed surface, and so on, until the next-to-last colored layer is hardened, whereupon the last molten material for the last colored layer can be poured into the remaining cavity and allowed to harden, and then the bar can be ejected from the mold.

In a manner similar to that described in U.S. Pat. No. 6,555,509 and U.S. Published Patent Application No. 2003/0199405, membrane separators which are at least partially water soluble or dispersible and which will dissolve or disintegrate with product use can be positioned between mold cavities to serve as barriers in the mold and thereby prevent fluid communication between the cavities, then flowable materials for forming different colored layers can be transferred to the cavities simultaneously or sequentially, then the flowable materials can be cooled simultaneously or sequentially until they are hardened, then the hardened, layered cleansing bar can be removed from the mold.

In a suitable extrusion process, in a manner similar to that described in U.S. Pat. No. 6,383,999, the various colored cleansing materials are separately prepared and plodded in such a way that the materials meet near the cone in the final plodder to give well separated stripes. The extruded product is subsequently cut and subjected to any other desired processing steps, such as pressing or stamping. It is contemplated that extrusion could be used to make, e.g., a bar of FIG. 3 or a bar of FIG. 4.

A suitable apparatus for manufacturing multicolored cleansing bars can be an apparatus like that described in U.S. Pat. No. 6,390,797, the disclosure of which is incorporated herein by reference.

In a preferred embodiment, the multicolored cleansing bar contains an object therein. The incorporation of an object in a cleansing bar is described in, e.g., U.S. Pat. No. 6,673,756, the disclosure of which is incorporated herein by reference.

Because children would be using the cleansing bar, in one embodiment of the present invention the object preferably is a toy. With a toy contained inside the cleansing bar, a child would be motivated to wash or bathe more with the cleansing bar so that he or she could obtain the toy. If the toy is directed to a boy or girl in particular, the cleansing bar could be identifiable at least at the outset by color. For example, if the toy inside is for a boy, the outside layer, top layer, or first layer could be purple, while if the toy inside is for a girl, the outside layer, top layer, or first layer could be red.

In another preferred embodiment, the object can be a prize identifier. For a rainbow colored cleansing bar, the prize identifier desirably can have the appearance of a pot of gold, which might represent a monetary prize to be used for education. Alternatively, as with the toy, the prize identifier could be for a prize directed to a boy or girl in particular, and the cleansing bar could be prepared accordingly.

The cleansing bar of the present invention can be used in a method for improving a child's hygiene, comprising (1) providing a child with a multicolored cleansing bar comprising a cleansing material and having a plurality of colors, and (2) having the child wash or bathe with the cleansing bar, wherein the child is motivated to wash or bathe with the cleansing bar in order to see the appearance of the cleansing bar change.

In this method, the cleansing bar can comprise a plurality of layers so that the color of the cleansing bar changes when a layer disappears due to washing or bathing.

Desirably, the plurality of layers in this method comprises at least a red layer, an orange layer, a yellow layer, a green layer, a blue layer, and a purple layer, because the these colors approximate the colors of a rainbow, and children like rainbows.

In the method of the present invention, the cleansing bar can comprise an outside layer and at least one inside layer, wherein the outside layer is a different color from at least one inside layer, thereby providing a pleasing color change effect for a child using the cleansing bar when a layer is used up.

Alternatively, in the method of the present invention, the cleansing bar can comprise a top layer and at least one other layer, wherein the top layer is a different color from at least one other layer, thereby providing a pleasing color change effect for a child when a layer is used up or, depending on the layer design, when the cleansing bar is rotated from top to bottom.

In the method of the present invention, when layers are present, they desirably are opaque, thereby enhancing the color change effect.

The method of the present invention can employ a cleansing bar which further comprises an antibacterial compound to enhance the benefits of the present invention.

In the method of the present invention, the cleansing bar desirably contains an object therein, preferably a toy or a prize identifier having the appearance of a pot of gold, to further motivate a child to wash or bathe.

In the present invention, the child can be a boy or girl twelve years of age or younger.

While the present invention has been described in detail and with reference to specific embodiments thereof, it will be apparent to one of ordinary skill in the art that various changes and modifications can be made therein without departing from the spirit and scope thereof.

What is claimed is:

1. A method for improving a child's hygiene, comprising (1) motivating a child to wash or bathe by providing the child with a multicolored cleansing bar comprising a cleansing material and having a plurality of colors designed to motivate the child to wash or bathe with the cleansing bar in order to see the appearance of the cleansing bar change, and (2) having the child wash or bathe with the cleansing bar, wherein the child is motivated to wash or bathe with the cleansing bar in order to see the appearance of the cleansing bar change, wherein the cleansing bar comprises an outside layer and at least one inside layer, wherein the outside layer is a different color from at least one inside layer, wherein the outside layer surrounds the at least one inside layer, wherein the layers are opaque, wherein the child sees the appearance of the cleansing bar change by washing or bathing with the cleansing bar so that the outside layer disappears due to the washing or bathing, thereby changing the color of the cleansing bar, and wherein the cleansing bar motivates the child to wash or bathe.

2. A method as in claim 1, wherein the cleansing bar comprises at least a red layer, an orange layer, a yellow layer, a green layer, a blue layer, and a purple layer.

3. A method as in claim 2, wherein the cleansing bar further comprises an antibacterial compound.

4. A method as in claim 2, wherein the cleansing bar contains an object therein.

5. A method as in claim 4, wherein the object is a toy.

6. A method as in claim 4, wherein the object is a prize identifier having the appearance of a pot of gold.

7. A method as in claim 1, wherein the cleansing bar further comprises an antibacterial compound.

8. A method as in claim 1, wherein the cleansing bar contains an object therein.

9. A method as in claim 8, wherein the object is a toy.

10. A method as in claim 8, wherein the object is a prize identifier having the appearance of a pot of gold.

11. The method as in claim 2, wherein the cleansing bar comprises an outside layer, a second layer which is adjacent to the outside layer, a third layer which is adjacent to the second layer, a fourth layer which is adjacent to the third layer, a fifth layer which is adjacent to the fourth layer, and a sixth layer which is adjacent to the fifth layer.

12. The method as in claim 11, wherein the outside layer is red.

13. The method as in claim 11, wherein the outside layer is purple.

14. The method as in claim 12, wherein the second layer is orange, the third layer is yellow, the fourth layer is green, the fifth layer is blue, and the sixth layer is purple.

15. The method as in claim 13, wherein the second layer is blue, the third layer is green, the fourth layer is yellow, the fifth layer is orange, and the sixth layer is red.

16. A method for improving a child's hygiene, comprising (1) motivating a child to wash or bathe by providing the child with a multicolored cleansing bar comprising a cleansing material and having a plurality of colors designed to motivate the child to wash or bathe with the cleansing bar in order to see the appearance of the cleansing bar change, and (2) having the child wash or bathe with the cleansing bar, wherein the child is motivated to wash or bathe with the cleansing bar in order to see the appearance of the cleansing bar change, wherein the cleansing bar comprises an outside layer and one inside layer, wherein the outside layer is a different color from the inside layer, wherein the outside layer surrounds the inside layer, wherein the layers are opaque, wherein the child sees the appearance of the cleansing bar change by washing or bathing with the cleansing bar so that the outside layer disappears due to the washing or bathing, thereby changing the color of the cleansing bar, and wherein the cleansing bar motivates the child to wash or bathe.

17. A method for motivating a child to wash or bathe with a cleansing bar in order to see the cleansing bar change color, comprising (1) motivating a child in need of motivation to wash or bathe by providing the child with a multicolored cleansing bar comprising a cleansing material and having a plurality of colors designed to motivate the child to wash or bathe with the cleansing bar in order to see the appearance of the cleansing bar change, and (2) having the child wash or bathe with the cleansing bar, wherein the child is motivated to wash or bathe with the cleansing bar in order to see the appearance of the cleansing bar change, wherein the cleansing bar comprises an outside layer and at least one inside layer, wherein the outside layer is a different color from at least one inside layer, wherein the outside layer surrounds the at least one inside layer, wherein the layers are opaque, wherein the child sees the appearance of the cleansing bar change by washing or bathing with the cleansing bar so that the outside layer disappears due to the washing or bathing, thereby changing the color of the cleansing bar, and wherein the cleansing bar motivates the child to wash or bathe.

* * * * *